US008324132B2

(12) United States Patent
Meredith et al.

(10) Patent No.: US 8,324,132 B2
(45) Date of Patent: Dec. 4, 2012

(54) MIXTURE AND METHOD FOR CONTROLLING UNDESIRED VEGETATION

(75) Inventors: Jeffrey Harve Meredith, Collierville, TN (US); Richard Manly Edmund, Jr., Little Rock, AR (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/076,997

(22) Filed: Mar. 31, 2011

(65) Prior Publication Data

US 2012/0252674 A1 Oct. 4, 2012

Related U.S. Application Data

(60) Provisional application No. 61/319,376, filed on Mar. 31, 2010.

(51) Int. Cl.
*A01N 57/00* (2006.01)
(52) U.S. Cl. ...................................................... 504/128
(58) Field of Classification Search ........................ None
See application file for complete search history.

(56) References Cited

U.S. PATENT DOCUMENTS

| | | | |
|---|---|---|---|
| 3,920,442 A | 11/1975 | Albert et al. | |
| 4,144,050 A | 3/1979 | Frensch et al. | |
| 4,383,113 A | 5/1983 | Levitt | |
| 4,405,531 A | 9/1983 | Franz | |
| 4,789,393 A | 12/1988 | Hanagan | |
| 5,260,260 A | 11/1993 | Gednalske et al. | |
| 5,599,769 A | 2/1997 | Hacker et al. | |
| 5,668,085 A | 9/1997 | Forbes et al. | |
| 6,159,900 A | 12/2000 | Beiringer et al. | |
| 6,316,386 B1 * | 11/2001 | Dahmen et al. | 504/128 |
| 2001/0031704 A1 | 10/2001 | Hacker et al. | |
| 2002/0198106 A1 | 12/2002 | Landes et al. | |
| 2007/0054805 A1 | 3/2007 | Krause et al. | |
| 2009/0209425 A1 | 8/2009 | Abraham et al. | |

FOREIGN PATENT DOCUMENTS

| | | |
|---|---|---|
| CN | 101548685 A | 10/2009 |
| DE | 3246493 A1 | 6/1984 |
| EP | 0318276 A1 | 5/1989 |
| WO | 9002486 A1 | 3/1990 |
| WO | 9113546 A1 | 9/1991 |
| WO | 9731535 A1 | 9/1997 |
| WO | 03024222 A1 | 3/2003 |
| WO | 2006034426 A1 | 3/2006 |
| WO | 2008155108 A2 | 12/2008 |

OTHER PUBLICATIONS

Kudsk, P., Mathiassen, S. K.; Joint Action of Amino Acid Biosynthesis-Inhibiting Herbicides; Weed Research; 2004, 44(4), 313-322; European Weed Research Society, Blackwell Publishing; U.K.

Devendra R. et al.; Quantification of Joint Action of Herbicides Mixture and Identification of Dosage for Control of Cyperus Rotundus L. and Oxalis Latifiolia H.B. & K; Proceedings of the Indian National Science Acadamy, Part B; Biological Sciences; 1997; 63(4); 349-358; Indian National Science Acadamy; India.

Eichhorn, M. M. Jr., Sanders, D. E.; Pensacola Bahiagrass Control in Coastal Bermudagrass Meadows; Proceedings of the Southern Weed Science Society; 1990; (Conference) Jan. 15, 16 & 17; (Abstract) 43, 142; 1990; Atlanta, Georgia; U.S.A.

Monks, C. D. et al.; Johnsongrass Response to Postemergence Herbicides Applied the Previous Year; Journal of Production Agriculture; 1998; 11(4); 507-509; U.S.A.

Kohrs, J. A. et al.; Sandbur Control in Bermudagrass Pastures and Hay Meadows; Proceedings to the ASA-CSSA-SSSA International Annual Meetings, Nov. 6-10, 2005; (Conference); Presented Nov. 7, 2005; Salt Lake City, Utah; U.S.A.

Montgomery, D. et al.; Evaluation of Nicosulfuron, Flazasulfuron and MSMA for Johnsongrass Control in Bermudagrass Roadsides; Annual Report for FY 2009; ODOT SPR Item No. 2157; Oklahoma Department of Transportation; Jan. 13, 2010; Oklahoma City, Oklahoma; U.S.A.

Horsley, S. B.; Tank Mixing Glyphosate With Adjuvant and Other Herbicides TOR Striped Maple Control; Proceedings of the Forty-Second Annual Meeting of the Northeastern Weed Science Society; Jan. 6, 7, & 8, 1988 (Conference); Hartford, Connecticut (Abstract); 42; College Park, Maryland; U.S.A.

Hacker, et al.; U.S. Appl. No. 08/050,291, filed Nov. 2, 1991.
Hacker, et al.; U.S. Appl. No. 08/231,999, filed Nov. 2, 1991.

* cited by examiner

*Primary Examiner* — Alton Pryor
(74) *Attorney, Agent, or Firm* — Reed A. Coats

(57) ABSTRACT

A herbicide mixture comprising nicosulfuron, metsulfuron-methyl and glyphosate is disclosed. A method for controlling undesired vegetation comprising contacting the undesired vegetation or its environment with a herbicidally effective amount of the herbicide mixture is also disclosed.

8 Claims, No Drawings

MIXTURE AND METHOD FOR CONTROLLING UNDESIRED VEGETATION

FIELD OF THE INVENTION

This invention relates to a mixture of certain herbicides and a method for using this mixture for controlling certain undesired vegetation.

BACKGROUND OF THE INVENTION

The control of undesired vegetation is extremely important in achieving healthy pasture, roadside, range and turf lands. Selective control of vegetation from the genus *Cenchrus* is particularly desirable where it is growing in stands of desired vegetation on these lands. Undesired vegetation from the genus *Cenchrus* is difficult to control using traditional chemical methods due to the close taxonomic relationship to surrounding desired vegetation. Once vegetation from the genus *Cenchrus* is established in pasture lands the value of the resulting hay produced by these lands is substantially reduced. The spiny burs (or pointy flowerets) on the vegetation from the genus *Cenchrus* get lodged in the mouths of livestock causing painful puncture wounds that affect the animal's desire to eat, thereby negatively affecting weight-gain. Vegetation from the genus *Cenchrus* also gets established in range lands where the spiny burs get caught in the wool of grazing sheep. Vegetation from the genus *Cenchrus* in turf lands (i.e. turf farms) reduces the value of the resulting sod. In all of these lands, but most particularly in pasture lands, few commercially available herbicides are available for controlling vegetation from the genus *Cenchrus*. The need continues for new herbicide treatments that are more effective, less costly, less toxic and environmentally safer.

SUMMARY OF THE INVENTION

This invention is directed to a herbicide mixture comprising nicosulfuron, metsulfuron-methyl and glyphosate. This invention also relates to a method for controlling undesired vegetation comprising contacting the undesired vegetation or its environment with a herbicidally effective amount of the herbicide mixture.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed. As referred to herein, the term "broadleaf" used either alone or in words such as "broadleaf weed" means dicot or dicotyledon, a term used to describe a group of angiosperms characterized by embryos having two cotyledons.

Nicosulfuron is commercially available in herbicidal compositions sold by a variety of companies including DuPont (e.g., ACCENT® Herbicide). Although nicosulfuron is most conveniently obtained as a commercial product, it can be prepared by methods described in U.S. Pat. No. 4,789,393.

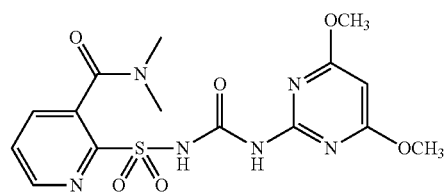

For the present invention, nicosulfuron may be provided by ACCENT® Herbicide as a 75% composition in the form of wettable granules.

Metsulfuron-methyl is commercially available in herbicidal compositions sold by a variety of companies including DuPont (e.g., ALLY® XP Herbicide, ESCORT® Herbicide). Although metsulfuron-methyl is most conveniently obtained as a commercial product, it can be prepared by methods described in U.S. Pat. No. 4,383,113.

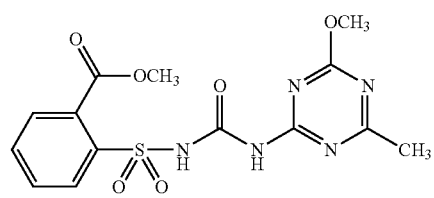

For the present invention, metsulfuron-methyl may be provided by ALLY® Herbicide as a 60% composition in the form of wettable granules.

Both nicosulfuron and metsulfuron-methyl are from the sulfonylurea class of herbicides acting by inhibiting acetohydroxy acid synthase (AHAS) (also known as acetolactate synthase (ALS)), and thus kill plants by inhibiting the production of branched-chain aliphatic amino acids such as valine, leucine and isoleucine, which are required for DNA synthesis and cell growth. These two herbicides are normally used individually to control certain weed species growing in row or rotational crops. Wettable granules of these herbicides can be formed as found in PCT publication WO 90/02486. Although mixtures of ALS inhibitors are known in the literature, surprising synergy can be observed when nicosulfuron and metsulfuron-methyl are mixed with glyphosate. A mixture of nicosulfuron and metsulfuron-methyl is made available under the trade name PASTORA® as sold by DuPont.

Glyphosate is commercially available in herbicidal compositions sold by a variety of companies including Monsanto (e.g., ROUNDUP® Herbicide). Although glyphosate is conveniently obtained as a commercial product, it can be prepared as described in U.S. Pat. Nos. 4,405,531 and 5,668,085.

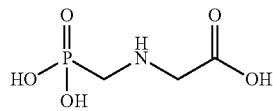

Ammonium salts of glyphosate are available commercially and can be purchased under the trade name "ROUNDUP®" or "ROUNDUP PRO CONCENTRATE®". For the present invention glyphosate may be provided by ROUNDUP POWERMAX® as the potassium salt in the form of a soluble liquid formulation. One skilled in the art recognizes that because in the environment and under physiological conditions salts and esters of chemical compounds are in equilibrium with their corresponding nonsalt and acidic forms, therefore, salts and esters share the biological utility of the nonsalt forms. Thus a wide variety of salts and esters of glyphosate are useful for controlling undesired vegetation. The salts of glyphosate are formed with organic or inorganic bases such as pyridine, triethylamine or ammonia, or amides, hydrides, hydroxides or carbonates of sodium, potassium, lithium, calcium, magnesium or barium. Accordingly, the present mixture and method comprises glyphosate and agriculturally suitable salts such as ammonium, isopropylammonium, potassium, sodium (including sesquisodium) and trimesium (alternatively named sulfosate) or esters thereof.

In the present disclosure and claims, the term "acid equivalent" and related terms such as "acid-equivalent basis" used to specify the amounts of a salt or ester of the glyphosate refers to the weight of glyphosate (i.e. the acid) corresponding in molar amount to the salt or ester. For example, glyphosate has a molecular weight of 169.07 g/mole, while its isopropyl ammonium salt has a molecular weight of 228.19 g/mole. So 228.19 g of the isopropyl ammonium salt can be said to be in the amount of 169.07 g on an acid-equivalent basis.

Glyphosate and salts and esters of glyphosate are best known as non-selective postemergence herbicides with a mode of action referred to as "EPSP (5-enol-pyruvylshikimate-3-phosphate) synthase inhibitors". These chemical compounds inhibit the enzyme 5-enol-pyruvylshikimate-3-phosphate synthase which is involved in the synthesis of aromatic amino acids such as tyrosine, tryptophan and phenylalanine EPSP inhibitors are readily absorbed through plant foliage and translocated in the phloem to the growing points.

Some vegetation is considered as undesirable vegetation when growing in pastures, hay fields and rangelands because of the mechanical injury that it inflicts on livestock. Woody stems, thorns, and stiff seed awns from the undesired vegetation from the genus *Cenchrus* cause injury to the mouth and digestive tract of livestock; and the hairs and fibers of some plants tend to ball up and obstruct the intestines causing serious problems. Barbed seed dispersal units may become so entangled in the wool of sheep so as to greatly diminish its market value.

Some vegetation is considered undesirable in roadside and turf lands because they detract from the visual uniformity normally associated with a manicured look. In roadside lands, johnsongrass (*Sorgham halepense*) presents a particular problem because it grows at a faster rate than desired vegetation such that it must be mowed more often. Johnsongrass quickly grows past regulation maximum height prescribed by some (U.S.) state highway mowing manuals when left unmowed. This causes a safety hazard due to the impairment of roadside lines of sight. Johnsongrass is also considered undesired vegetation in roadside lands because it out-competes desired vegetation.

In the present disclosure and claims, "turf" refers to the locus of a layer comprising grass plants with roots and root-entrained growing medium (e.g., soil) attached. In the present disclosure and claims, the term "turfgrass" refers to bunch and sod-forming grass species and varieties that have foliage and growth habits suitable for periodically mowed turf used for golf courses and other sporting areas and lawns. Furthermore, where vegetation from the genus *Cenchrus* gets established on public turf lands such as golf courses, college campuses, public gardens, public parks, sporting fields and the like, the spiny burs can cause puncture wounds to humans.

As is generally understood in the art, control of undesired vegetation includes killing or injuring the undesired vegetation or reducing its growth. For example, applying a herbicidally effective amount of the herbicide mixture by the present method, control typically involves killing undesired vegetation to remove these plants as competitors for water, nutrients, sunlight and growing space, as well as providing a homogenous appearance to the desired vegetation. Also in the context of the present invention where cultivation or grazing is intended, control of undesired vegetation includes killing plants that are either unhealthy for, can cause injury to, or reduce the weight-gain of the livestock that consumes the surrounding desired vegetation.

In the present disclosure, "insignificant injury" to bermudagrass is the amount of slight injury (e.g., growth reduction or change in color) generally noticeable only to a person professionally trained in chemical weed control and not to an untrained person (e.g., homeowner), who would typically not regard the bermudagrass appearance as unusual. In contrast, "significant injury" to bermudagrass is noticeable by most people. Significant injury can include major growth reduction (difference between treated and untreated), easily noticeable yellowing of bermudagrass (chlorosis) or browning of bermudagrass (necrosis). In the present method, injury to bermudagrass is evaluated visually and assigned a phytotoxic response rating using a 0-100 scale. Although a lower rating on bermudagrass is considered advantageous, a visual rating of about 20 or lower is considered an acceptable injury rating before cut and harvest. Therefore, one particular aspect of the present mixture and method is the excellent safety to bermudagrass.

The present mixture can be applied according to the present method during either the active growing or dormant periods of the desired vegetation. Applications made during the active growing period are typically made within about three days to about 21 days after cut and harvest. More typically, the application will be made within about four days to about 14 days after cut and harvest and most typically within about 7 days. Application of the present mixture according to the present method is followed by a second cut and harvest of the desired vegetation from about 16 days to about 50 days after application. Typically the second cut and harvest is made about 18 to about 40 days after application and most typically between about 19 and about 31 days after application. Therefore one aspect of the present mixture and method is the synergistic control of undesired vegetation during these time periods.

As described above, the present mixture can be applied according to the present method during the dormant period of the desired vegetation. Although the desired vegetation is dormant, the undesired vegetation may be actively growing. Therefore, another aspect of this invention is the control of undesirered vegetation actively growing in dormant desired vegetation. In particular, rescuegrass (*Bromus catharticus* Vahl.) growing in dormant bermudagrass is controlled by the present mixture and method. Application of the present mixture according to the present method during dormant periods of desired vegetation are typically done in anticipation of the active growing period of the desired vegetation. Application during the dormant period (i.e. in advance of "green-up") can minimize any injury (phytotoxicity) to the desired vegetation. Application of the present mixture according to the present method during dormant periods of the desired vegetation are typically followed by a primary cut and harvest of the desired vegetation from about 30 days to about 65 days after application. More typically the primary cut and harvest is made about 45 to about 61 days after application and most typically between about 50 and about 61 days after application.

Embodiments of the present invention as described in the Summary of the Invention include:

Embodiment A1. The herbicide mixture described in the Summary of the Invention comprising nicosulfuron, metsulfuron-methyl, glyphosate and a liquid diluent.

Embodiment A2. The herbicide mixture of Embodiment A1 comprising nicosulfuron, metsulfuron-methyl, glyphosate, a liquid diluent and a non-ionic surfactant.

Embodiment A3. The herbicide mixture of Embodiment A1 comprising nicosulfuron, metsulfuron-methyl, glyphosate, a liquid diluent and a crop oil concentrate.

Embodiment A4. The herbicide mixture of any one of Embodiments A1 through A3 wherein glyphosate comprises the potassium salt of glyphosate.

Embodiment A5. The herbicide mixture of any one of Embodiments A1 through A4 wherein the nicosulfuron comprises nicosulfuron supplied for the herbicide mixture as wettable granules.

Embodiment A6. The herbicide mixture of any one of Embodiments A1 through A5 wherein metsulfuron-methyl comprises metsulfuron-methyl supplied for the herbicide mixture as wettable granules.

Embodiment A7. The herbicide mixture of any one of Embodiments A1 through A6 wherein nicosulfuron comprises 75% nicosulfuron supplied for the herbicide mixture as wettable granules.

Embodiment A8. The herbicide mixture of any one of Embodiments A1 through A7 wherein metsulfuron-methyl comprises 60% metsulfuron-methyl supplied for the herbicide mixture as wettable granules.

Embodiment A9. The herbicide mixture of any one of Embodiments A1 through A8 wherein the liquid diluent comprises water.

Embodiment A10. The herbicide mixture described in the Summary of the Invention or any one of Embodiments A1 through A9 wherein the ratio of nicosulfuron to metsulfuron-methyl is from about 10:1 to about 0.5:1.

Embodiment A11. The herbicide mixture of Embodiment A10 wherein the ratio of nicosulfuron to metsulfuron-methyl is from about 9:1 to about 1:1.

Embodiment A12. The herbicide mixture of Embodiment A11 wherein the ratio of nicosulfuron to metsulfuron-methyl is from about 7:1 to about 2:1.

Embodiment A13. The herbicide mixture of Embodiment A12 wherein the ratio of nicosulfuron to metsulfuron-methyl is from about 4:1 to about 3:1.

Embodiment A14. The herbicide mixture of Embodiment A13 wherein the ratio of nicosulfuron to metsulfuron-methyl is about 3.75:1.

Embodiment A15. The herbicide mixture described in the Summary of the Invention or any one of Embodiments A1 through A14 further comprising a non-ionic surfactant or a crop oil concentrate.

Embodiment A16. The herbicide mixture of any one of Embodiment A1 through A15 further comprising a non-ionic surfactant.

Embodiment A17. The herbicide mixture described in the Summary of the Invention or any one of Embodiments A1 through A16 wherein the ratio of nicosulfuron to metsulfuron-methyl to glyphosate is from about 4:1:50 to about 3:1:50.

Embodiment A18. The herbicide mixture of Embodiment A11 wherein the ratio of nicosulfuron to metsulfuron-methyl to glyphosate is from about 4:1:20 to about 3:1:20.

Embodiment A19. The herbicide mixture of Embodiment A18 wherein the ratio of nicosulfuron to metsulfuron-methyl to glyphosate is from about 4:1:5 to about 3:1:5

Embodiment A20. The herbicide mixture as described in the Summary of the Invention or any one of Embodiments A1 through A19 wherein the ratio of nicosulfuron to metsulfuron-methyl to glyphosate is from about 3.75:1:40 to about 3.75:1:1.

Embodiment A21. The herbicide mixture of Embodiment A20 wherein the ratio of nicosulfuron to metsulfuron-methyl to glyphosate is from about 3.75:1:30 to about 3.75:1:3.

Embodiment A22. The herbicide mixture of Embodiment A21 wherein the ratio of nicosulfuron to metsulfuron-methyl to glyphosate is from about 3.75:1:28 to about 3.75:1:18.

Embodiment A23. The herbicide mixture described in the Summary of the Invention or any one of Embodiments A1 through A22 wherein the herbicide mixture is a synergistic herbicide mixture.

Embodiment B1. The method described in the Summary of the Invention wherein the contacting comprises applying the herbicide mixture as a spray-mixture to the undesired vegetation.

Embodiment B2. The method of Embodiment B1 wherein the spray-mixture is prepared from a pre-mixture comprising nicosulfuron and metsulfuron-methyl.

Embodiment B3. The method of any one of Embodiments B1 through B2 wherein the spray-mixture is prepared from a first-mixture comprising nicosulfuron, metsulfuron-methyl and a liquid diluent.

Embodiment B4. The method of any one of Embodiments B1 through B2 wherein the spray-mixture is prepared from a first-mixture comprising glyphosate and a liquid diluent.

Embodiment B5. The method described in the Summary of the Invention or any one of Embodiments B1 through B3 wherein the spray-mixture is prepared by adding glyphosate to a pre-mixture comprising nicosulfuron and metsulfuron-methyl prior to applying.

Embodiment B6. The method described in the Summary of the Invention or any one of Embodiments B1 through B4 wherein the spray-mixture is prepared by adding a pre-mixture comprising nicosulfuron and metsulfuron-methyl to glyphosate prior to applying.

Embodiment B7. The method of Embodiment B6 wherein the spay-mixture is prepared by adding a liquid diluent to a pre-mixture comprising nicosulfuron and metsulfuron-methyl.

Embodiment B8. The method of Embodiment B7 wherein the spray-mixture is prepared by adding glyphosate to a first-mixture comprising nicosulfuron, metsulfuron-methyl and a liquid diluent.

Embodiment B9. The method of Embodiment B8 wherein the spray-mixture is prepared by adding glyphosate to a first-mixture comprising nicosulfuron as 75% nicosulfuron and metsulfuron-methyl as 60% metsulfuron-methyl.

Embodiment B10. The method of Embodiment B9 wherein the spray-mixture is prepared by adding glyphosate to a first-mixture comprising nicosulfuron as 75% nicosulfuron formulated as wettable granules and metsulfuron-methyl as 60% metsulfuron-methyl formulated as wettable granules.

Embodiment B11. The method described in the Summary of the Invention or any one of Embodiments B1 through B10 wherein the liquid diluent comprises water.

Embodiment C1. The method described in the Summary of the Invention or any one of Embodiments B1 through B11 wherein the undesired vegetation is from the genus *Cenchrus*, *Sorghum* or *Setaria*.

Embodiment C2. The method described in the Summary of the Invention or any one of Embodiments B1 through B11 or C1 wherein the undesired vegetation is other than from the genus *Sorghum* or *Setaria*.

Embodiment C3. The method described in the Summary of the Invention or any one of Embodiments B1 through B11 or Embodiment C1 or C2 wherein the undesired vegetation is from the genus *Cenchrus*.

Embodiment C4. The method described in the Summary of the Invention or any one of Embodiments C1 through C3 wherein the undesired vegetation from the genus *Cenchrus* is selected from kamanomano (*C. agrimonioides* (var. *kamanomano* Trin.) or *C. agrimonioides* (var. *laysanensis* Trin.)), slimbristle sandbur (*C. brownii*, Roem. & Schult.), southern sandbur (*C. echinatus* L. or *C. brevisetus* Fourn), coastal sandbur (*C. humilis* Hitchc.), longspine sandbur, mat-sandbur or mat-sandbur grass (*C. longispinus* (Hack.) Fernald), field sandbur (*C. incertus* M. A. Curtis or *C. pauciflorus* Benth.) and sand-dune sandbur (*C. macrocephalus*, *C. tribuloides* L. or *C. vaginatus*).

Embodiment C5. The method of Embodiment C4 wherein the undesired vegetation from the genus *Cenchrus* is selected from kamanomano (*C. agrimonioides* (var. *kamanomano* Trin.) or *C. agrimonioides* (var. *laysanensis* Trin.)), slimbristle sandbur (*C. brownii*, Roem. & Schult.), southern sandbur (*C. echinatus* L. or *C. brevisetus* Fourn), coastal sandbur (*C. humilis* Hitchc.), longspine sandbur, mat-sandbur or mat-sandbur grass (*C. longispinus* (Hack.) Fernald), field sandbur (*C. incertus* M. A. Curtis or *C. pauciflorus* Benth.) and sand-dune sandbur (*C. macrocephalus*, *C. tribuloides* L. or *C. vaginatus*).

Embodiment C6. The method of Embodiment C5 wherein the undesired vegetation is selected from the group consisting of longspine sandbur, mat-sandbur or mat-sandbur grass (*C. longispinus* (Hack.) Fernald) and field sandbur (*C. incertus* M. A. Curtis or *C. pauciflorus* Benth.).

Embodiment C7. The method of Embodiment C6 wherein the undesired vegetation is selected from the group consisting of *C. longispinus* (Hack.) Fernald (i.e. longspine sandbur) and *C. incertus* M. A. Curtis (i.e. field sandbur).

Embodiment C8. The method described in the Summary of the Invention or any one of Embodiments C1 through C7 wherein the undesired vegetation is a perennial species.

Embodiment C9. The method described in the Summary of the Invention or any one of Embodiments C1 through C8 wherein the undesired vegetation is other than a perennial species.

Embodiment C10. The method described in the Summary of the Invention or any one of Embodiments C1 through C9 wherein the undesired vegetation is growing in bermudagrass (*Cynodon dactylon*).

Embodiment C11. The method described in the Summary of the Invention or any one of Embodiments B1 through B11 wherein the undesired vegetation is selected from the genus *Bromus*, *Cenchrus*, *Sorghum* and *Setaria*.

Embodiment C12. The method Embodiment C11 wherein the undesired vegetation is selected from the genus *Bromus*.

Embodiment C13. The method Embodiment C12 wherein the undesired vegetation is *Bromus catharticus* (i.e. rescuegrass).

Embodiments of this invention, including Embodiments A1-A25, B1-B11 and C1-C13 above as well as any other embodiments described herein, can be combined in any manner, and the descriptions of the embodiments pertain not only to the mixture but also to the method.

Combinations of Embodiments A1-A25, B1-B11 and C1-C13 are illustrated by the following embodiments:

Embodiment D1. The herbicide mixture as described in the Summary of the Invention wherein the ratio of nicosulfuron to metsulfuron-methyl is from about 10:1 to about 0.5:1

Embodiment D2. The method described in the Summary of the Invention wherein the contacting comprises applying the herbicide mixture as a spray-mixture to the undesired vegetation.

Embodiment D3. The method described in Embodiment D2 wherein the spray-mixture is prepared by adding glyphosate to a pre-mixture comprising nicosulfuron and metsulfuron-methyl prior to applying.

Embodiment D4. The method of Embodiment D2 wherein the contacting comprises applying the spray-mixture to the undesired vegetation selected from the genus *Bromus, Cenchrus, Sorghum* or *Setaria*.

Embodiment D5. The method of Embodiment D4 wherein the contacting comprises applying the spray-mixture to the undesired vegetation selected from the genus *Cenchrus* and *Setaria*.

Embodiment D6. The method of Embodiment D5 wherein the contacting comprises applying the spray-mixture to the undesired vegetation from the genus *Cenchrus*.

Embodiment D7. The method of Embodiment D6 wherein the contacting comprises applying the spray-mixture to the undesired vegetation selected from the group consisting of *Cenchrus longispinus, Cenchrus incertus* and *Cenchrus pauciflorus*.

Embodiment D8. The method of Embodiment D7 wherein the undesired vegetation is selected from the group consisting of *Cenchrus longispinus* and *Cenchrus incertus*.

Embodiment D9. The method of Embodiment D8 wherein the undesired vegetation is growing in *Cynodon dactylon*.

One or more of the following methods and variations thereof as described below can be used to prepare the mixture and use the present method as described in the Summary of the Invention.

The herbicidal mixture can usually be prepared just prior to use, however, some parts of the mixture can be prepared ahead of time and are made available to use as the pre-mixture. For the present mixture and method, the term "pre-mixture" is the combined components comprising nicosulfuron and metsulfuron-methyl. For example, wettable granules of nicosulfuron (75% active ingredient) and wettable granules of metsulfuron-methyl (60% active ingredient) are available separately for use to control certain weed species in row or rotational crops. The use of these two active ingredients together simultaneously in the present mixture and method was previously not advised due to either lack of registration or at least one of the two individual components previously being inappropriate for use in pasture, range, roadside or turf lands. A mixture of wettable granules comprising nicosulfuron and metsulfuron-methyl can be combined in one package to provide the pre-mixture of the present mixture and suitable for the present method. This pre-mixture, when prepared according to the present mixture and method can contain varying amounts of the two components. Most preferably the pre-mixture comprises 56% nicosulfuron and 15% metsulfuron-methyl. It is most convenient to purchase this pre-mixture as made available under the trade name PASTORA® and sold by DuPont.

For the present mixture and method, the term "first-mixture" comprises glyphosate and a liquid diluent. Preferred for the present mixture and method is the first-mixture comprising the pre-mixture (i.e. comprising nicosulfuron and metsulfuron-methyl) and a liquid diluent. Also preferred for the mixture and method of the present method is to add the pre-mixture (i.e. comprising nicosulfuron and metsulfuron-methyl) as wettable granules to a liquid diluent to prepare a "first-mixture". The components of the pre-mixture are generally formulated as wettable granules and can be added to any liquid diluent in a suitable spray tank. The final volume of the first-mixture should not exceed the total volume of the tank in order to accommodate any additional components of the first-mixture to provide the resulting spray-mixture.

For the present mixture and method, the term "spray-mixture" comprises the three components of the herbicide mixture in a liquid diluent suitable for spray application. Although the three components of the mixture can be combined in any order, there are two principle ways to prepare the spray-mixture. If the first-mixture comprises glyphosate and a liquid diluent, the remaining parts of the herbicide mixture (i.e. the pre-mixture) can be added to the first-mixture as wettable granules. Preferred for the present mixture and method, is where the first-mixture comprises the pre-mixture and a liquid diluent and glyphosate (formulated as a soluble liquid) is added to the first-mixture. Therefore, the spray-mixture is generally prepared by adding the pre-mixture components (i.e. comprising nicosulfuron and metsulfuron-methyl) to a liquid diluent to prepare a first-mixture, and glyphosate is subsequently added to prepare a spray-mixture. This general process is known as tank mixing. Any optional formulation auxiliaries or additives are generally added to the first mixture to provide the spray-mixture. Although the present mixture and method optionally includes a crop oil or non-ionic surfactant, there is no requirement to include these components.

For the present invention, the term "undesired vegetation" refers to vegetation that is rooted in areas where it is not desired. Reasons vegetation might be undesired include, for example, because the vegetation is an invasive species, it disturbs the local flora, robs nutrients from surrounding flora, does not provide the desired root structure for soil support, presents a safety hazard, can cause injury to livestock or pedestrians, or is a nuisance for some other reason. Hard to control vegetation such as knotroot foxtail (*Setaria geniculata* (Lam.) Beauv.), johnsongrass (*Sorgham halepense*), rescuegrass (*Bromus catharticus* Vahl.) and vaseygrass (*Paspalum urvillei*), particularly knotroot foxtail and rescugrass can be controlled by the present mixture and method. Undesired vegetation from the genus *Cenchrus* is particularly well controlled. Undesired vegetation from the genus *Cenchrus* which is controlled by the present invention includes: kamanomano (*C. agrimonioides* (var. *kamanomano* Trin.) or *C. agrimonioides* (var. *laysanensis* Trin.)), Indian sandbur (*C. barbatus* Schumach. or *C. biflorus* Roxb.), slimbristle sandbur (*C. brownii*, Roem. & Schult.), buffel grass (*C. ciliari, C. cilié* or *C. de Rhodésie*), southern sandbur (*C. echinatus* L. or *C. brevisetus* Fourn), slender sandbur (*C. gracillimus* Nash), pitscale grass (*C. granularis* L. Kuntze), coastal sandbur (*C. humilis* Hitchc.), coastal sandbur (*C. spinifex* Cay.), longspine sandbur, mat-sandbur or mat-sandbur grass (*C. longispinus* (Hack.) Fernald), big sandbur or giant *cenchrus* (*C. myosuroides* Kunth), field sandbur (*C. incertus* M. A. Curtis or *C. pauciflorus* Benth.), sanddune sandbur (*C. macrocephalus, C. tribuloides* L. or *C. vaginatus*), birdwood grass (*C. setiger* or *C. setigerus* Vahl), Mossman River grass (*C. quinquevalvis* Buch.-Ham ex. Wall) also *C. australis* R. Br., *C. carolinianus* Walt., *C. calyculatus* Cav., *C. catharticus* Delisle, *C. inflexus* R. Br., *C. lappaceus* L., *C. leptacanthus* A. Camus, *C. pennisetiformis, C. perinvolucratus* Stapf & C. E. Hubb., *C. pilosus* Kunth, *C. prieurii, C. pungens* Kunth, *C. racemosus* L. and *C. viridis*.

The present invention controls undesired vegetation from the genus *Cenchrus* selected from the group consisting of: kamanomano (*C. agrimonioides* (var. *kamanomano* Trin.) or *C. agrimonioides* (var. *laysanensis* Trin.)), slimbristle sandbur (*C. brownii*, Roem. & Schult.), southern sandbur (*C. echinatus* L. or *C. brevisetus* Fourn), coastal sandbur (*C. humilis* Hitchc.), field sandbur (*C. incertus* M. A. Curtis or *C. pauciflorus* Benth.), longspine sandbur, mat-sandbur or mat-sandbur grass (*C. longispinus* (Hack.) Fernald) and sanddune sandbur (*C. macrocephalus, C. tribuloides* L. or *C. vaginatus*). The present invention controls undesired vegetation from the genus *Cenchrus* selected from the group consisting of: field sandbur (*C. incertus* M. A. Curtis or *C. pauciflorus* Benth.) and longspine sandbur, mat-sandbur or mat-sandbur grass (*C. longispinus* (Hack.) Fernald).

For the present method, the term "desired vegetation" refers to vegetation that is rooted in areas where it is desired because it serves a desired purpose for example feeding livestock or preventing erosion of the growing medium. For the present invention, typical desired vegetation found in pasture land (or hay-grass growing in pasture land) includes, but is not limited to, bermudagrass (*C. dactylon*). Typical desired vegetation growing in turf lands includes a range of grass species and hybrid species including Kentucky bluegrass, St. Augustine grass, Kentucky fescue and Bermuda grass, *Axonopus fissifolius* (Raddi) Kuhlm. (also known as *Axonopus affinis* Chase, Common carpetgrass), *Bouteloua dactyloides* (Nutt.) J. T. Columbus (also known as *Buchloe dactyloides* (Nutt.) Engelm., Buffalograss), *Cynodon dactylon* (L.) Pers. (Common Bermudagrass, Bermudagrass), *Cynodon dactylon* (L.) Pers. x *C. transvaalensis* Burtt-Davy (Hybrid Bermudagrass), *Eremochloa ophiuroides* (Munro) Hack. (Centipede grass, Common Centipedegrass), *Paspalum notatum* Flueggé. (Bahiagrass), *Paspalum vaginatum* Sw. (Seashore *paspalum*), *Stenotaphrum secundatum* (Walter) Kuntze (St. Augustine grass, St. Augustinegrass), *Zoysia japonica* Steud. (Korean lawngrass, Japanese lawngrass), *Zoysia matrella* (L.) Merr. (Manila grass) and *Zoysia tenuifolia* Willd. ex Thiele (Mascarene grass). Desired vegetation well suited for use with the present invention is the species selected from bermudagrass (*Cynodon dactylon*).

The spray-mixture of the present invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

As the mixture and method of the present invention have postemergent herbicidal activity, to control undesired vegetation by killing or injuring the undesired vegetation or reducing its growth, the mixture and method can be usefully applied by a variety of methods involving contacting a herbicidally effective amount of the mixture of the invention, or applying by the present method with at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

Application of the spray-mixture is generally performed with hydraulic handgun sprayers, backpack sprayers, field sprayers, boom sprayers and sprayers for aerial application from fixed wing and rotor aircraft. Pressure for propelling the spray-mixture can be provided by gasses under pressure (i.e. $CO_2$ for small volumes) or by pumps to pressurize the spray-mixture contained in the spray-tank to the desired pressure. Any propellants or pumps elevate the pressure of the spray-mixture to the desired level for a proper spray pattern. Most preferred for the present mixture and method is where the spray-mixture is applied by a field sprayer or boom sprayer appropriate for commercial application.

Additional components selected from the group consisting of surfactants, solid diluents and liquid diluents, may also serve as a carrier. The formulation or composition ingredients are selected to be consistent with the physical properties of the active ingredient, mode-of-application and environmental factors such as soil type, moisture and temperature.

The first-mixture is typically extended in a suitable medium before spraying (usually water). Spray volumes can range from about one to several thousand liters per hectare, but more typically are in the range from about ten to several hundred liters per hectare. The first-mixture can be mixed with a liquid diluent (e.g., water) or another suitable medium to prepare the spray-mixture for foliar application by aerial or ground application, or for application to the growing medium of the plant. Application performed by aerial application can use final spray-mixture volumes of up to about 70 liters (about 2.472 cubic feet) per hectare, but more typically from about 28 to about 47 liters (about 0.9888 to about 1.66 cubic feet) per hectare. Application performed by ground application can require final spay-mixture volumes of about 500 liters (about 17.66 cubic feet) per hectare, but more typically from about 50 to about 200 liters (about 1.766 to about 7.063 cubic feet) per hectare.

Although a spray-mixture formed by diluting the pre-mixture with water at sufficient concentration before addition of glyphosate can provide sufficient efficacy for controlling undesired vegetation, separately formulated adjuvant products can also be added to the spray-mixture. These additional adjuvants are commonly known as "spray adjuvants" or "tank mix adjuvants", and include any substance mixed in a spray tank to improve the performance of a pesticide application, such as by enhancing efficacy (e.g., biological availability, adhesion, penetration, uniformity of coverage and durability of protection), or minimizing or eliminating spray application problems associated with incompatibility, foaming, drift, evaporation, volatilization and degradation. As no single adjuvant generally can provide all these benefits, compatible adjuvants are often combined to perform multiple functions. To obtain optimal performance, adjuvants are selected with regard to the properties of the active ingredient, formulation and target (i.e. undesired vegetation growing in desired vegetation).

Among the spray adjuvants, oils including crop oils, crop oil concentrates, vegetable oil concentrates and methylated seed oil concentrates are most commonly used to improve the efficacy of pesticides, possibly by means of promoting more even and uniform spray deposits. In situations where phytotoxicity of desired vegetation potentially caused by oils or other water-immiscible liquids are of concern, spray compositions prepared from the composition of the present invention will generally not contain oil-based spray adjuvants. However, in situations where phytotoxicity of desired vegetation caused by oil-based spray adjuvants is commercially insignificant, spray compositions prepared from the composition of the present composition can also contain oil-based spray adjuvants, which can potentially further increase control of undesired vegetation, as well as rainfastness.

Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of nonionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of nonionic surfactants. Adjuvant performance can be improved by replacing the vegetable oil with methyl esters of fatty acids that are typically derived from vegetable oils. Examples of methylated seed oil concentrates include MSO® Concentrate from UAP-Loveland Products, Inc. and Premium MSO Methylated Spray Oil from Helena Chemical Company. The amount of oil-based adjuvants added to the spray-mixture generally does not exceed about 2.5% by volume, and more typically the amount is from about 0.1 to about 1% by volume. The application rates of oil-based adjuvants added to the spray-mixture are typically between about 1 to about 5 L (about 0.03531 to about 0.1766 cubic feet) per hectare, and methylated seed oil-based adjuvants in particular are typically used at a rate from about 1 to about 2.5 L (about 0.03531 to about 0.08829 cubic feet) per hectare.

Spray adjuvants containing oils, with or without emulsifiers, particularly methylated seed oils, are compatible in tank mixtures with the present mixture and method. Therefore one embodiment of the present invention relates to a mixture or method for controlling undesired vegetation, further comprising adding to the first-mixture an adjuvant such as a methylated seed oil (in any order of addition or mixing) or adding an adjuvant such as a methylated seed oil (in any order of addition or mixing) to the spray-mixture, and contacting the undesired vegetation or its environment with a herbicidally effective amount of the spray-mixture.

The ratio of the volume of the pre-mixture to the volume of water used to dilute it is generally in the range from about 1:100 to about 1:1000, more typically from about 1:200 to about 1:800, and most typically from about 1:300 to about 1:600. The amount of diluted pre-mixture needed for effective control of undesired vegetation (i.e. a herbicidally effective amount) depends upon a variety of factors including the concentration of pre-mixture, glyphosate, presence and concentration of any other adjuvants, the extent of dilution in water, the susceptibility of undesired vegetation and the environment. These conditions can be easily determined by calculation and simple experimentation by one skilled in the art. A herbicidally effective amount of the present mixture and method of this invention is determined by a number of factors. These factors include: method of application, amount and type of vegetation present, growing conditions, etc. In general, a herbicidally effective amount of the mixture and method of this invention is about 0.001 to 20 kg/ha with a preferred range of about 0.004 to 1 kg/ha. One skilled in the art can easily determine the herbicidally effective amount necessary for the desired level of weed control.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

Wettable granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Water-dispersible and water-soluble granules can be prepared as taught in U.S. Pat. No. 4,144,050, U.S. Pat. No. 3,920,442 and DE 3,246,493.

When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents. Surfactants can be classified as nonionic, anionic or cationic. Nonionic surfactants are the most useful for the present mixture and method for reasons of cost and availability. Nonionic surfactants include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

One skilled in the art will understand that the present mixture used according to the present method will not be synergistic on all species of undesired vegetation growing in desired vegetation. Nevertheless, it is believed that test results will indicate that the herbicide mixture, when used according to the present method will be highly active postemergent on certain species of undesired vegetation. Furthermore, the mixture and method shows synergism to control undesired vegetation from the genus *Cenchrus*.

The herbicide mixture and method of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. The herbicide mixture and method of the invention with other herbicides can broaden the spectrum of activity against additional undesired vegetation, and suppress the proliferation of any resistant biotypes. Thus the present invention also pertains to a herbicide mixture and method and at least one additional biologically active compound or agent (in a biologically effective amount) and can further comprise at least one of a surfactant, a solid diluent or a liquid diluent. The other biologically active compounds or agents can be formulated with the herbicide mixture and method comprising nicosulfuron, metsulfuron-methyl, glyphosate include at least one of a surfactant, solid or liquid diluent. For the herbicide mixture and the method comprising one or more other biologically active compounds or agents can be formulated together with the herbicide mixture to form a pre-mixture or one or more other biologically active compounds or agents can be formulated separately from the herbicide mixture and method and the formulations combined together before application (e.g., in a spray tank) or, alternatively, applied in succession.

Addition of one of the following herbicides into the present mixture or method may be particularly useful for controlling undesired vegetation growing in desired vegetation: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clefoxydim, clethodim, clodinafop-propargyl, clomazone, clomeprop, clopyralid, clopyralid-olamine, cloransulam-methyl, cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethamethryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxapropethyl, fenoxaprop-P-ethyl, fenoxasulfone, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, fluorochloridone, fluoroxypyr, flurtamone, fluthiacet-methyl, fomesafen, foramsulfuron, fosamine-ammonium, glufosinate, glufosinate-ammonium, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, molinate, monolinuron, naproanilide, napropamide, naptalam, neburon, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufenethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butyl.) Butyl. and *Puccinia thlaspeos* Schub.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to nicosulfuron is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of undesired vegetation controlled beyond the spectrum controlled by the present method and mixture alone.

In certain instances, combinations of the present mixture and method of this invention with other biologically active (particularly herbicidal) compounds or agents (i.e. active ingredients) can result in a greater-than-additive (i.e. synergistic) effect on undesired vegetation and/or a less-than-additive effect (i.e. safening) on desired vegetation. Reducing the quantity of active ingredients released in the environment while ensuring effective pest control is always desirable. Ability to use greater amounts of active ingredients to provide more effective control of desired vegetation without excessive injury to desired vegetation is also desirable. When synergism of herbicidal active ingredients occurs on undesired vegetation at application rates giving agronomically satisfactory levels of control, such combinations can be advantageous for reducing desired vegetation production cost and decreasing environmental load. When safening of herbicidal active ingredients occurs on desired vegetation, such combinations can be advantageous for increasing desired vegetation protection by reducing competition.

Of note is a combination of the present mixture and method of the invention with at least one other herbicidal active ingredient. Of particular note is such a combination where the other herbicidal active ingredient has a different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Without further elaboration, it is believed that one skilled in the art using the preceding description can utilize the present invention to its fullest extent. The following Examples are, therefore, to be construed as merely illustrative and not limiting of the disclosure in any way whatsoever. The following Tests demonstrate the control efficacy of the mixture and method of this invention against specific undesired vegetation. The control afforded by the present mixture and method is not limited, however, to these species.

Biological Examples of the Invention

Test A

Herbicide mixtures were applied on Jul. 24, 2009 to 28 m² plots of bermudagrass (*Cynodon dactylon*, CYNDA) near De Leon, Tex. to control field sandbur (*Cenchrus incertus* M. A. Curtis, CCHIN) approximately one week after the bermudagrass had been cut and harvested. All herbicides were formulated in water containing either 0.25% (vol/vol) non-ionic surfactant ("NIS" provided by INDUCE®) or 1.0% (vol/vol) crop oil concentrate ("COC" provided by Agri-Dex®) and applied to bermudagrass stubble using a backpack sprayer pressurized with $CO_2$. Crop phytotoxic response (% phyto) and weed control efficacy (% control) were visually evaluated twenty days after the mixtures were applied using a 0-100 scale where zero is no visible response and 100 is plant death. In the following table "g a.i./ha" means grams active ingredient per hectare.

TABLE A1

Bermudagrass (CYNDA) and Field Sandbur (CCHIN) Responses to Combinations of Nicosulfuron, Metsulfuron-Methyl and Glyphosate

| Nicosulfuron (g a.i./ha) | Metsulfuron-methyl (g a.i./ha) | Glyphosate* (g a.i./ha) | Adjuvant | CYNDA (% phyto) | CCHIN (% control) |
|---|---|---|---|---|---|
| 39.4 | 10.5 | 0 | NIS | 8.3 | 43.3 |
| 59.1 | 15.8 | 0 | COC | 8.3 | 46.7 |
| 39.4 | 10.5 | 96.6 | NIS | 8.3 | 63.3 |
| 39.4 | 10.5 | 192.5 | NIS | 13.3 | 92.7 |
| 39.4 | 10.5 | 289.1 | NIS | 21.7 | 97.7 |

*Glyphosate provided by the potassium salt of glyphosate.

Test B

Herbicide mixtures were applied on Jul. 22, 2009 to 185 m² plots of bermudagrass (*Cynodon dactylon*, CYNDA) near Iowa, La. to control vaseygrass (*Paspalum urvillei*, PASUR) and johnsongrass (*Sorghum halapense*, SORHA) approximately one week after the bermudagrass had been cut and harvested. All herbicides were formulated in water containing 1.0% (vol/vol) crop oil concentrate (provided by Agri-Dex®) and applied to bermudagrass stubble using a backpack sprayer pressurized with $CO_2$. Crop phytotoxic response (% phyto) and weed control efficacy (% control) were visually evaluated forty-four days after herbicides were applied using a 0-100 scale where zero is no visible response and 100 is plant death. In the following table "g a.i./ha" means grams active ingredient per hectare.

TABLE B1

Bermudagrass (CYNDA), Vaseygrass (PASUR), and Johnsongrass (SORHA) Responses to Combinations of Nicosulfuron, Metsulfuron-methyl and Glyphosate

| Nicosulfuron (g a.i./ha) | Metsulfuron-methyl (g a.i./ha) | Glyphosate* (g a.i./ha) | CYNDA (% phyto) | PASUR (% control) | SORHA (% control) |
|---|---|---|---|---|---|
| 59.1 | 15.8 | 0 | 0 | 80 | 85 |
| 59.1 | 15.8 | 48.3 | 0 | 75 | 90 |
| 59.1 | 15.8 | 96.6 | 0 | 70 | 90 |
| 59.1 | 15.8 | 192.5 | 0 | 80 | 80 |

*Glyphosate provided by the potassium salt of glyphosate.

In the following Tests C through E, Colby's equation was used to calculate the expected additive herbicidal effect of nicosulfuron and glyphosate alone and in combination. Colby's equation (S. R. Colby, "Calculating Synergistic and Antagonistic Responses of Herbicide Combinations," *Weeds*, 15(1), pp 20-22 (1967)) calculates the expected additive effect of herbicidal mixtures, and for two active ingredients is of the form:

$$P_{a+b} = P_a + P_b - (P_a P_b / 100)$$

wherein $P_{a\pm b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

For mixtures comprising nicosulfuron, metsulfuron-methyl and glyphosate the expected herbicidal effect was calculated based on the combination of nicosulfuron and metsulfuron-methyl providing observed herbicidal effect $P_a$ and glyphosate providing observed herbicidal effect $P_b$ in the Colby Equation. Plant responses to components $P_a$ and $P_b$ range from zero to 100% where zero is no observed response and 100% is complete response (i.e. plant death). Mixtures of herbicides were tested for their ability to express synergism (enhanced weed control) or antagonism (improved tolerance) at several locations in the United States. In the following Tests glyphosate was provided by the potassium salt of glyphosate. Crop phytotoxic response (% phyto) and weed control efficacy (% control) were visually evaluated using a 0-100 scale where zero is no visible response and 100 is plant death. In the following Tables "DAA" means days after application and "g a.i./ha" means grams active ingredient per hectare.

Test C

Herbicides and herbicide mixtures were applied to field plots of bermudagrass (*Cynodon dactylon*, CYNDA) near De Leon, Tex., Yukon, Okla. and Burlington, Okla. to control field sandbur (*Cenchrus incertus* M. A. Curtis, CCHIN) approximately one week after the bermudagrass had been cut and harvested. All herbicides and herbicide mixtures were formulated in water containing 0.25% (vol/vol) non-ionic surfactant ("NIS" provided by INDUCE®) and applied as a spray mixture to bermudagrass stubble using a backpack sprayer pressurized with $CO_2$.

TABLE C1

Effect of Nicosulfuron and Glyphosate Alone, in Combination and in Mixtures with Metsulfuron-methyl on Bermudagrass (CYNDA) and Sandbur (CCHIN) 15 DAA near De Leon, TX.

| Nicosulfuron (g a.i./ha) | Metsulfuron-methyl (g a.i./ha) | Glyphosate (g a.i./ha) | CYNDA (% phyto) Expected | CYNDA (% phyto) Observed | CCHIN (% control) Expected | CCHIN (% control) Observed |
|---|---|---|---|---|---|---|
| 39 | 0 | 0 | — | 5 | — | 65 |
| 39 | 10.5 | 0 | — | 7 | — | 59 |
| 0 | 0 | 96 | — | 0 | — | 60 |
| 0 | 0 | 192 | — | 5 | — | 74 |
| 0 | 0 | 289 | — | 13 | — | 89 |
| 39 | 0 | 96 | 5 | 8 | 86 | 60 |
| 39 | 0 | 192 | 10 | 8 | 91 | 83 |
| 39 | 0 | 289 | 25 | 7 | 96 | 92 |
| 39 | 10.5 | 96 | 7 | 7 | 84 | 75 |
| 39 | 10.5 | 192 | 12 | 10 | 89 | 89 |
| 39 | 10.5 | 289 | 19 | 8 | 95 | 96 |

TABLE C2

Effect of Nicosulfuron and Glyphosate Alone, in Combination and in Mixtures with Metsulfuron-methyl on Bermudagrass (CYNDA) and Sandbur (CCHIN) 30 DAA near Yukon, OK.

| Nicosulfuron (g a.i./ha) | Metsulfuron-methyl (g a.i./ha) | Glyphosate (g a.i./ha) | CYNDA (% phyto) Expected | CYNDA (% phyto) Observed | CCHIN (% control) Expected | CCHIN (% control) Observed |
|---|---|---|---|---|---|---|
| 39 | 0 | 0 | — | 10 | — | 78 |
| 39 | 10.5 | 0 | — | 10 | — | 80 |
| 0 | 0 | 96 | — | 0 | — | 2 |
| 0 | 0 | 192 | — | 0 | — | 18 |
| 0 | 0 | 289 | — | 0 | — | 35 |
| 39 | 0 | 96 | 10 | 10 | 78 | 80 |
| 39 | 0 | 192 | 10 | 10 | 82 | 84 |
| 39 | 0 | 289 | 10 | 10 | 86 | 87 |
| 39 | 10.5 | 96 | 10 | 0 | 80 | 92 |
| 39 | 10.5 | 192 | 10 | 10 | 84 | 92 |
| 39 | 10.5 | 289 | 10 | 18 | 87 | 94 |

TABLE C3

Effect of Nicosulfuron and Glyphosate Alone, in Combination and in Mixtures with Metsulfuron-methyl on Bermudagrass (CYNDA) and Sandbur (CCHIN) 90 DAA near Yukon, OK and Burlington, OK.

| Nicosulfuron (g a.i./ha) | Metsulfuron-methyl (g a.i./ha) | Glyphosate (g a.i./ha) | CYNDA (% phyto) Expected | CYNDA (% phyto) Observed | CCHIN (% control) Expected | CCHIN (% control) Observed |
|---|---|---|---|---|---|---|
| 39 | 0 | 0 | — | 0 | — | 88 |
| 39 | 10.5 | 0 | — | 0 | — | 90 |
| 0 | 0 | 96 | — | 0 | — | 55 |
| 0 | 0 | 192 | — | 0 | — | 63 |
| 0 | 0 | 289 | — | 0 | — | 75 |
| 39 | 0 | 96 | 0 | 0 | 95 | 98 |
| 39 | 0 | 192 | 0 | 0 | 96 | 96 |
| 39 | 0 | 289 | 0 | 0 | 97 | 98 |
| 39 | 10.5 | 96 | 0 | 0 | 96 | 96 |
| 39 | 10.5 | 192 | 0 | 0 | 96 | 96 |
| 39 | 10.5 | 289 | 0 | 0 | 98 | 98 |

Test D

Herbicides and herbicide mixtures were applied to field plots of bermudagrass (*Cynodon dactylon*, CYNDA) near Lena, Miss. and Paris, Ark. to control knotroot foxtail (*Setaria geniculata* [Lam.] Beauv., SETGE) approximately one week after the bermudagrass had been cut and harvested. All herbicides and herbicide mixtures were formulated in water containing 0.25% (vol/vol) non-ionic surfactant ("NIS" provided by INDUCE®) and applied to bermudagrass stubble as a spray mixture using a backpack sprayer pressurized with $CO_2$.

TABLE D1

Effect of Nicosulfuron and Glyphosate Alone, in Combination and in Mixtures with Metsulfuron-methyl on Bermudagrass (CYNDA) and Knotroot Foxtail (SETGE) 15 DAA near Lena, MS.

| Nicosulfuron | Metsulfuron-methyl | Glyphosate | CYNDA (% phyto) | | SETGE (% control) | |
|---|---|---|---|---|---|---|
| (g a.i./ha) | (g a.i./ha) | (g a.i./ha) | Expected | Observed | Expected | Observed |
| 39 | 10.5 | 0 | — | 20 | — | 93 |
| 59 | 17.5 | 0 | — | 28 | — | 96 |
| 0 | 0 | 192 | — | 18 | — | 79 |
| 0 | 0 | 289 | — | 20 | — | 84 |
| 39 | 10.5 | 192 | 34 | 22 | 99 | 97 |
| 39 | 10.5 | 289 | 36 | 23 | 99 | 97 |
| 59 | 17.5 | 192 | 40 | 27 | 99 | 97 |
| 59 | 17.5 | 192 | 42 | 27 | 99 | 96 |

TABLE D2

Effect of Nicosulfuron and Glyphosate Alone, in Combination and in Mixtures with Metsulfuron-methyl on Bermudagrass (CYNDA) and Knotroot Foxtail (SETGE) 30 DAA near Paris, AR.

| Nicosulfuron | Metsulfuron-methyl | Glyphosate | CYNDA (% phyto) | | SETGE (% control) | |
|---|---|---|---|---|---|---|
| (g a.i./ha) | (g a.i./ha) | (g a.i./ha) | Expected | Observed | Expected | Observed |
| 39 | 0 | 0 | — | 3 | — | 28 |
| 39 | 10.5 | 0 | — | 2 | — | 27 |
| 0 | 0 | 96 | — | 0 | — | 7 |
| 0 | 0 | 192 | — | 2 | — | 28 |
| 0 | 0 | 289 | — | 11 | — | 40 |
| 39 | 0 | 96 | 3 | 2 | 33 | 28 |
| 39 | 0 | 192 | 5 | 8 | 48 | 40 |
| 39 | 0 | 289 | 14 | 13 | 57 | 57 |
| 39 | 10.5 | 96 | 2 | 4 | 32 | 33 |
| 39 | 10.5 | 192 | 4 | 10 | 47 | 61 |
| 39 | 10.5 | 289 | 13 | 13 | 56 | 66 |

TABLE D3

Effect of Nicosulfuron and Glyphosate Alone, in Combination and in Mixtures with Metsulfuron-methyl on Bermudagrass (CYNDA) and Knotroot Foxtail (SETGE) 60 DAA near Paris, AR.

| Nicosulfuron | Metsulfuron-methyl | Glyphosate | CYNDA (% phyto) | | SETGE (% control) | |
|---|---|---|---|---|---|---|
| (g a.i./ha) | (g a.i./ha) | (g a.i./ha) | Expected | Observed | Expected | Observed |
| 39 | 0 | 0 | — | 0 | — | 10 |
| 39 | 10.5 | 0 | — | 0 | — | 10 |
| 0 | 0 | 96 | — | 0 | — | 3 |
| 0 | 0 | 192 | — | 0 | — | 18 |
| 0 | 0 | 289 | — | 0 | — | 20 |
| 39 | 0 | 96 | 0 | 0 | 13 | 10 |
| 39 | 0 | 192 | 0 | 0 | 26 | 18 |
| 39 | 0 | 289 | 0 | 0 | 28 | 22 |
| 39 | 10.5 | 96 | 0 | 0 | 13 | 12 |
| 39 | 10.5 | 192 | 0 | 0 | 26 | 22 |
| 39 | 10.5 | 289 | 0 | 0 | 28 | 23 |

Test E

Herbicides and herbicide mixtures were applied to field plots of dormant bermudagrass (*Cynodon dactylon*, CYNDA) near Eatonton, Ga. on Mar. 20, 2010 and Decatur, Tex. on Mar. 30, 2010 to control rescuegrass (*Bromus catharticus* Vahl., BROCA). All herbicides and herbicide mixtures were formulated in water containing 1.0% (vol/vol) crop oil concentrate and applied as a spray mixture to bermudagrass using a backpack sprayer pressurized with $CO_2$.

TABLE E1

Effect of Nicosulfuron and Glyphosate Alone, in Combination and in Mixtures with Metsulfuron-methyl on Rescuegrass (BROCA) 15 DAA near Eatonton, GA.

| Nicosulfuron | Metsulfuron-methyl | Glyphosate | BROCA (% control) | |
|---|---|---|---|---|
| (g a.i./ha) | (g a.i./ha) | (g a.i./ha) | Expected | Observed |
| 39 | 0 | 0 | — | 10 |
| 39 | 10.5 | 0 | — | 0 |
| 0 | 0 | 144 | — | 0 |
| 0 | 0 | 289 | — | 87 |
| 39 | 0 | 144 | 10 | 10 |
| 39 | 0 | 289 | 88 | 96 |
| 39 | 10.5 | 144 | 0 | 93 |
| 39 | 10.5 | 289 | 87 | 95 |

TABLE E2

Effect of Nicosulfuron and Glyphosate Alone, in Combination and in Mixtures with Metsulfuron-methyl on Bermudagrass (CYNDA) and Rescuegrass (BROCA) 30 DAA near Decatur, TX.

| Nicosulfuron | Metsulfuron-methyl | Glyphosate | CYNDA (% phyto) | | BROCA (% control) | |
|---|---|---|---|---|---|---|
| (g a.i./ha) | (g a.i./ha) | (g a.i./ha) | Expected | Observed | Expected | Observed |
| 39 | 0 | 0 | — | 0 | — | 63 |
| 39 | 10.5 | 0 | — | 0 | — | 83 |
| 0 | 0 | 144 | — | 0 | — | 0 |
| 0 | 0 | 289 | — | 0 | — | 0 |
| 39 | 0 | 144 | 0 | 0 | 63 | 93 |
| 39 | 0 | 289 | 0 | 0 | 63 | 93 |
| 39 | 10.5 | 144 | 0 | 0 | 83 | 90 |
| 39 | 10.5 | 289 | 0 | 0 | 83 | 92 |

TABLE E3

Effect of Nicosulfuron and Glyphosate Alone, in Combination and in Mixtures with Metsulfuron-methyl on Bermudagrass (CYNDA) and Rescuegrass (BROCA) 45 DAA near Eatonton, GA.

| Nicosulfuron | Metsulfuron-methyl | Glyphosate | CYNDA (% phyto) | | BROCA (% control) | |
|---|---|---|---|---|---|---|
| (g a.i./ha) | (g a.i./ha) | (g a.i./ha) | Expected | Observed | Expected | Observed |
| 39 | 0 | 0 | — | 0 | — | 79 |
| 39 | 10.5 | 0 | — | 0 | — | 27 |
| 0 | 0 | 144 | — | 0 | — | 88 |
| 0 | 0 | 289 | — | 0 | — | 95 |
| 39 | 0 | 144 | 0 | 0 | 97 | 92 |
| 39 | 0 | 289 | 0 | 0 | 99 | 96 |
| 39 | 10.5 | 144 | 0 | 0 | 91 | 92 |
| 39 | 10.5 | 289 | 0 | 0 | 96 | 99 |

TABLE E4

Effect of Nicosulfuron and Glyphosate Alone, in Combination and in Mixtures with Metsulfuron-methyl on Bermudagrass (CYNDA) and Rescuegrass (BROCA) 60 DAA near Decatur, TX.

| Nicosulfuron (g a.i./ha) | Metsulfuron-methyl (g a.i./ha) | Glyphosate (g a.i./ha) | CYNDA (% phyto) | | BROCA (% control) | |
|---|---|---|---|---|---|---|
| | | | Expected | Observed | Expected | Observed |
| 39 | 0 | 0 | — | 0 | — | 53 |
| 39 | 10.5 | 0 | — | 0 | — | 40 |
| 0 | 0 | 144 | — | 0 | — | 0 |
| 0 | 0 | 289 | — | 0 | — | 0 |
| 39 | 0 | 144 | 0 | 0 | 53 | 57 |
| 39 | 0 | 289 | 0 | 0 | 53 | 75 |
| 39 | 10.5 | 144 | 0 | 0 | 40 | 78 |
| 39 | 10.5 | 289 | 0 | 0 | 40 | 87 |

What is claimed is:

1. A method for controlling undesired vegetation selected from the genus *Bromus, Cenchrus, Sorghum* and *Setaria* growing in *Cynodon dactylon* comprising contacting the undesired vegetation or its environment with a herbicidally effective amount of a herbicide mixture comprising nicosulfuron, metsulfuron-methyl and glyphosate.

2. The method of claim 1 wherein the undesired vegetation is selected from the genus *Bromus*.

3. The method of claim 2 wherein the undesired vegetation is *Bromus catharticus*.

4. The method of claim 1 wherein the undesired vegetation is selected from the genus *Cenchrus, Sorghum* or *Setaria*.

5. The method of claim 4 wherein the undesired vegetation is selected from the genus *Cenchrus* and *Setaria*.

6. The method of claim 5 wherein the undesired vegetation is selected from the genus *Cenchrus*.

7. The method of claim 6 wherein the undesired vegetation is selected from the group consisting of *Cenchrus longispinus, Cenchrus incertus* and *Cenchrus pauciflorus*.

8. The method of claim 7 wherein the undesired vegetation is selected from the group consisting of *Cenchrus longispinus* and *Cenchrus incertus*.

* * * * *